US009903832B2

(12) United States Patent
Chen et al.

(10) Patent No.: US 9,903,832 B2
(45) Date of Patent: Feb. 27, 2018

(54) METHODS FOR MEASURING ANALYTE CONCENTRATION

(71) Applicant: Industrial Technology Research Institute, Hsinchu (TW)

(72) Inventors: Chu-Hsuan Chen, Zhubei (TW); Yu-Fang Yen, Hsinchu (TW); Yi-Yen Yuan, Zhubei (TW); Hui-Ju Shen, Tainan (TW); Fen-Fei Lin, Zhudong Township (TW); Yi-Ting Tung, Tainan (TW); Wen-Pin Hsieh, Sanwan Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 301 days.

(21) Appl. No.: 14/839,345

(22) Filed: Aug. 28, 2015

(65) Prior Publication Data

US 2016/0320327 A1 Nov. 3, 2016

Related U.S. Application Data

(60) Provisional application No. 62/153,647, filed on Apr. 28, 2015.

(51) Int. Cl.
*C12Q 1/00* (2006.01)
*G01N 27/327* (2006.01)
*G01N 27/48* (2006.01)

(52) U.S. Cl.
CPC ..... *G01N 27/3274* (2013.01); *G01N 27/3272* (2013.01); *G01N 27/48* (2013.01)

(58) Field of Classification Search
CPC . G01N 27/3274; G01N 27/3272; G01N 27/48
See application file for complete search history.

(56) References Cited

U.S. PATENT DOCUMENTS 6,890,421 B2 5/2005 Ohara et al.
7,018,843 B2 3/2006 Heller
(Continued)

FOREIGN PATENT DOCUMENTS

CN 1815236 A 8/2006
CN 103901092 A 7/2014
(Continued)

OTHER PUBLICATIONS

Extended European Search Report, dated Sep. 29, 2016, for European Application No. 15182945.4.
Barreau et al., "Effect of Hematocrit Concentration on Blood Glucose Value Determined on Glucometer II", Diabetes Care, vol. 11, No. 2, Feb. 1988, pp. 116-118.
(Continued)

*Primary Examiner* — Jayne L Mershon
(74) *Attorney, Agent, or Firm* — Birch, Stewart, Kolasch & Birch, LLP

(57) ABSTRACT

The present disclosure provides a method for detecting an analyte concentration. The method includes providing a test strip, which includes a first electrode set including a first reaction area, a second electrode set including a second reaction area, and a reaction reagent layer disposed on the second reaction area. The method includes providing a blood sample and bringing the blood sample into contact with the first electrode set and the second electrode set, applying a first voltage to the first electrode set by voltammetry to obtain a first response value, calculating a hematocrit value according to the first response value, applying a second voltage to the second electrode set to obtain a second response value, and calculating the actual value of the analyte concentration by using the hematocrit value and the second response value.

17 Claims, 11 Drawing Sheets

(56) References Cited

U.S. PATENT DOCUMENTS

| | | | |
|---|---|---|---|
| 7,258,769 B2* | 8/2007 | Cui | B01L 3/502715 |
| | | | 204/403.01 |
| 7,390,667 B2 | 6/2008 | Burke et al. | |
| 7,638,033 B2 | 12/2009 | Kasielke et al. | |
| 7,699,973 B2 | 4/2010 | Tonks | |
| 8,287,717 B2 | 10/2012 | Wu | |
| 8,293,096 B2 | 10/2012 | Cardosi et al. | |
| 8,404,100 B2 | 3/2013 | Wu | |
| 8,409,424 B2 | 4/2013 | Chen et al. | |
| 8,540,864 B2 | 9/2013 | Fujiwara et al. | |
| 8,617,369 B2 | 12/2013 | Tonks | |
| 8,623,660 B2 | 1/2014 | Kraft et al. | |
| 8,691,072 B2 | 4/2014 | Fujiwara et al. | |
| 8,691,075 B2 | 4/2014 | Lica | |
| 8,709,739 B2 | 4/2014 | Chatelier et al. | |
| 2004/0157339 A1* | 8/2004 | Burke | G01N 27/3274 |
| | | | 436/149 |
| 2007/0235346 A1 | 10/2007 | Popovich et al. | |
| 2008/0083618 A1 | 4/2008 | Neel et al. | |
| 2011/0139634 A1* | 6/2011 | Chou | G01N 27/3274 |
| | | | 205/792 |
| 2013/0098776 A1 | 4/2013 | Hsu | |
| 2013/0180869 A1 | 7/2013 | Liao et al. | |
| 2013/0199943 A1 | 8/2013 | Craggs et al. | |
| 2013/0341186 A1 | 12/2013 | Hsu | |
| 2014/0178909 A1 | 6/2014 | Tonks | |
| 2014/0224672 A1* | 8/2014 | Hsu | C12Q 1/001 |
| | | | 205/777.5 |

FOREIGN PATENT DOCUMENTS

| | | |
|---|---|---|
| EP | 2 799 855 A1 | 11/2014 |
| TW | 201350840 A | 12/2013 |
| TW | I464397 B | 12/2014 |
| WO | WO 2004/113910 A1 | 12/2004 |
| WO | WO 2011/030093 A1 | 3/2011 |

OTHER PUBLICATIONS

Ginsberg, "Factors Affecting Blood Glucose Monitoring: Sources of Errors in Measurement", Journal of Diabetes Science and Technology, vol. 3, Issue 4, Jul. 2009, pp. 903-913.

Holtzinger et al., "Evaluation of a New POCT Bedside Glucose Meter and Strip With Hematocrit and Interference Corrections", Point of Care, vol. 7, No. 1, Mar. 2008, pp. 1-6.

Hui et al., "Impedance study of erythrocyte aggregation and sedimentation by piezoelectric crystal sensor", Bioelectrochemistry and Bioenergetics, vol. 36, 1995, pp. 161-164.

Lee et al., "Development of Hematocrit Monitoring Sensor Using Screen Printed Carbon Electrode", Transducers 2013, Jun. 16-20, 2013, pp. 2165-2168.

Müller et al., "Influence of Hematocrit and Platelet Count on Impedance and Reactivity of Whole Blood for Electrical Aggregometry", Journal of Pharmacological and Toxicological Methods, vol. 34, No. 1, Sep. 1995, pp. 17-22.

Musholt et al., "Dynamic Electrochemistry Corrects for Hematocrit Interference on Blood Glucose Determinations with Patient Self-Measurement Devices", Journal of Diabetes Science and Technology, vol. 5, Issue 5, Sep. 2011, pp. 1167-1175.

Pop et al., "Blood Electrical Impedance Closely Matches Whole Blood Viscosity as Parameter of Hemorheology and Inflammation", Applied Rheology, vol. 13, Issue 6, 2003 (Final version Oct. 23, 2003), pp. 305-312.

Tanaka et al., "Continuous Monitoring of Circulating Blood Hematocrit", Jap. J. Physiol., vol. 26, 1976 (received for publication Jan. 7, 1976), pp. 345-353.

Teodorczyk et al., "Hematocrit Compensation in Electrochemical Blood Glucose Monitoring Systems", Journal of Diabetes Science and Technology, vol. 6, Issue 3, May 2012, pp. 648-655.

Treo et al., "Hematocrit Measurement by Dielectric Spectroscopy", IEEE Transactions on Biomedical Engineering, vol. 52, No. 1, Jan. 2005, pp. 124-127.

* cited by examiner

METHODS FOR MEASURING ANALYTE CONCENTRATION

TECHNICAL FIELD

The present disclosure relates to a method for detecting analyte concentration, and in particular it relates to a method for detecting analyte concentration which is capable of calibrating a hematocrit (Hct) value.

DESCRIPTION OF THE RELATED ART

A hematocrit value refers to the proportion of red blood cells within a certain amount of blood. More specifically, the hematocrit value mainly refers to the detected proportion that the precipitated blood cells (mainly red blood) occupy in the whole blood after the anticoagulated whole blood is centrifuged. The more the red blood cells exit after the centrifugation, the higher the hematocrit value is, which represents a lower proportion occupied by the plasma. The less the red blood cells exit after the centrifugation, the lower the hematocrit value is, which represents a higher proportion occupied by the plasma. For normal adults, the hematocrit values of an average male is 40% to 50%, and the hematocrit values of an average female is 35% to 45%. The value is affected by gender, age, physical condition, and dietary intake. For many patients, it is common to have a broader hematocrit distribution, of lower than 20% and higher than 60%.

Conventionally, the plasma is used as the test sample for detectors used in the clinical laboratories. That is, the blood is centrifuged first, then the resulting plasma is used to conduct the test. As such, the detection results do not suffer from the interference of the difference of the hematocrit values. However, opposite to the large equipment used in the clinical laboratory, the whole blood sample from patients are usually adopted as test samples for point-of-care-testing (POCT) devices, or meters which patients can operate themselves (over-the-counter; OTC). If the plasma and the blood cells have to be separated to obtain the plasma to conduct the test, more volume of the whole blood sample is needed for the plasma isolation and purification, which raises the difficulties for patients who wish to operate the detectors by themselves. It also increases the cost of the detectors, and increases the time required for detection. Therefore, typically, most of the point-of-care-testing (POCT) devices, or the meters which patients can operate by themselves (OTC) use the whole blood samples from patients to conduct a direct measurement. However, in such cases, detection interference is caused by the hematocrit levels with individual differences.

Take the blood glucose test strip as an example, different hematocrit levels cause different effects. For example, if the hematocrit level is too low, it is easy to cause the measured glucose concentration to be too high; if the hematocrit level is too high, it will cause the measured glucose concentration to be too low. Therefore, it is very important to the detection system to provide a system and method for calibration to make the detection bias resulting from the hematocrit value of the sample be correctly calibrated.

After blood glucose meters have become more popular, the Food and Drug Administration (FDA) published draft guidelines on January, 2014, in which the hematocrit (Hct) value is first considered as interfering items to the blood glucose meters. Thus, the hematocrit value is formally included as an interfering item which has to be considered in examination reports for the sale of the blood glucose meters. The draft also mentions that, in the future, companies will have to use clinical samples with hematocrit values in a range of 10% to 65% in the submitted product acceptance test for sale.

Therefore, an improved method for detecting analyte concentration is needed. Except for correctly calibrating the bias that is a result of the hematocrit values, the hematocrit range to be tested in the samples may conform to the request for the glucose meter for selling in the future.

SUMMARY

In one embodiment, the present disclosure provides a method for detecting an analyte concentration, which includes providing a test strip. The test strip includes a first electrode set including a first reaction area; a second electrode set including a second reaction area; and a reaction reagent layer disposed on the second reaction area. The method includes providing a blood sample and bringing the blood sample into contact with the first electrode set and the second electrode set; applying a first voltage to the first electrode set by voltammetry to obtain a first response value; calculating a hematocrit value according to the first response value; applying a second voltage to the second electrode set to obtain a second response value; and calculating the actual value of the analyte concentration by using the hematocrit value and the second response value.

In another embodiment, the present disclosure also provides a method for detecting an analyte concentration, which includes providing a test strip. The test strip includes a first electrode set including a first reaction area; a second electrode set including a second reaction area; and a reaction reagent layer disposed on the second reaction area. The method includes providing a blood sample and bringing the blood sample into contact with the first electrode set and the second electrode set; obtaining a hematocrit value by using the first electrode set; conducting a calibration to a linear equation related with the analyte concentration by using the hematocrit value to obtain a calibrated linear equation; applying a voltage to the second electrode set to obtain a response value; and calculating the actual value of the analyte concentration using the response value and the calibrated linear equation.

A detailed description is given in the following embodiments with reference to the accompanying drawings.

DETAILED DESCRIPTION OF DISCLOSED EMBODIMENTS

The present disclosure provides method for detecting the analyte concentration. The detection bias that is a result of the hematocrit values of the sample can be correctly calibrated using this method.

Figure 1:
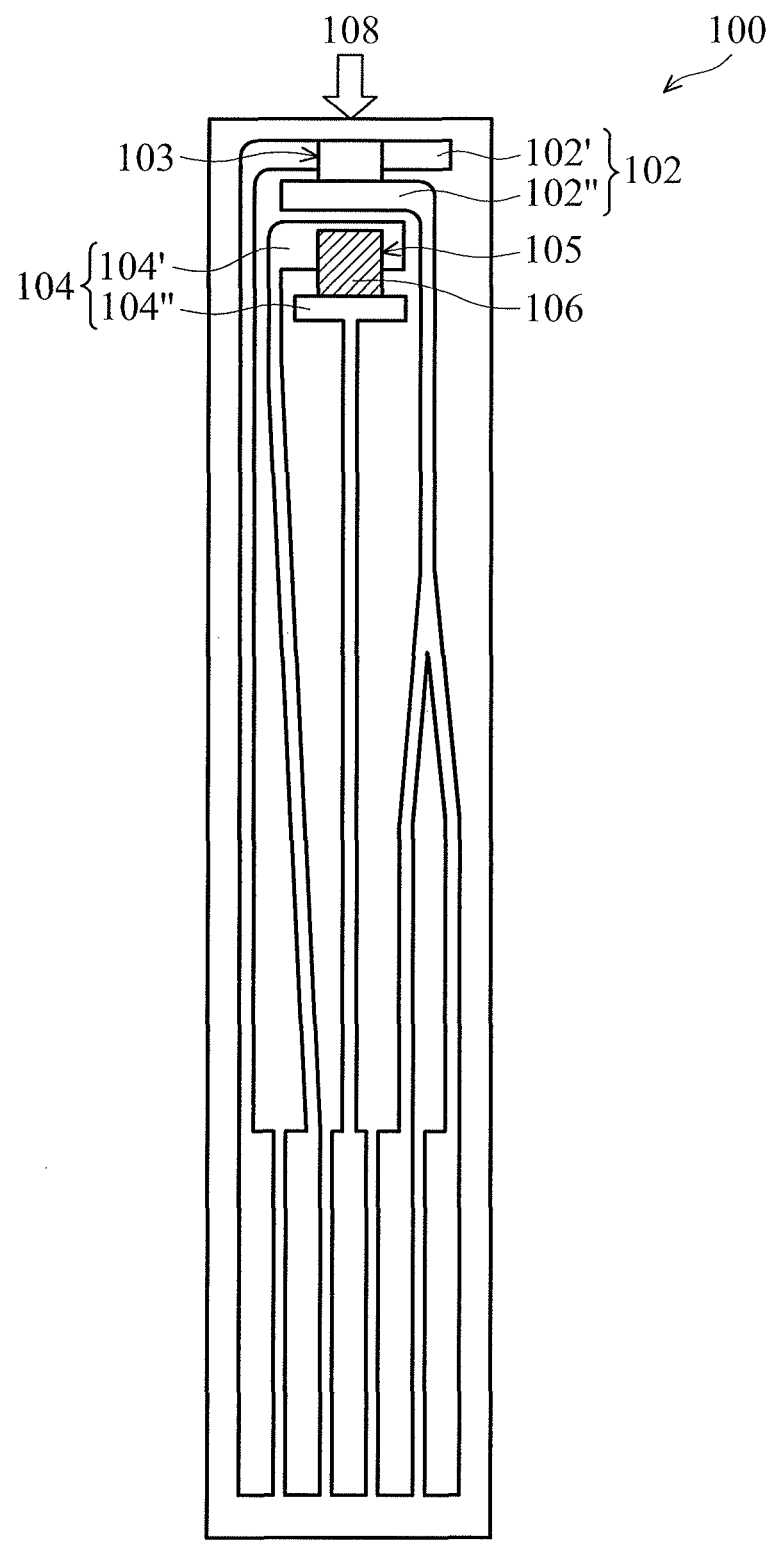
FIG. 1 illustrates a schematic diagram of a test strip according to an embodiment of the present disclosure.

FIG. 1 illustrates a schematic diagram of a test strip 100 according to an embodiment of the present disclosure. In one embodiment, the present disclosure provides a test strip 100 including a first electrode set 102, a second electrode set 104, and a reaction reagent layer 106. The first electrode set 102 may include a first reaction area 103, and the second electrode set 104 may include a second reaction area 105, and the first reaction area 103 and the second reaction area 105 are disposed in the same channel. However, as will be realized by those skilled in the art, the above arrangement may include other variations. For example, the first reaction area and the second reaction area may respectively be disposed in different channels.

In one embodiment, the first electrode set 102 may be composed of a working electrode 102' and a reference electrode 102", and the second electrode set 104 may be composed of a working electrode 104' and a reference electrode 104". As shown in FIG. 1, in this embodiment, the first electrode set 102 may be disposed at the end relatively proximal to the sample inlet 108, and the second electrode set 104 may be disposed at the end relatively distal to the sample inlet 108. However, as will be realized by those skilled in the art, the above arrangement may include other variations. For example, the proximal and distal ends are disposed oppositely, at left and right, or on different planes. As long as the first electrode set or the second electrode set can come into contact with the blood to conduct the test, any arrangement can be used in the present disclosure. In another embodiment, the reference electrode 102" of the first electrode set 102 and the reference electrode 104" of the second electrode set 104 may be electrically connected. Alternatively, in still another embodiment, the first electrode set 102 and the second electrode set 104 may have a common reference electrode.

It should be noted that, according to an embodiment of the present disclosure, the reference electrode 104" is disposed at the end relatively distal to the sample inlet of the test strip. As shown in FIG. 1, when the two electrode sets 102, 104 respectively includes the working electrodes 102', 104' and the reference electrodes 102", 104", or when the reference electrodes 102", 104" are electrically connected, the reference electrode 104" can further be used to detect the entrance of the sample. As such, the function of detection can be started when the sample is enough, so a more precise detection can be achieved. According to another embodiment of the present disclosure, when the first electrode set 102 and the second electrode set 104 have a common reference electrode, this common reference electrode can also be used to detect the entrance of the sample, and the function of detection can be started when an enough blood sample is detected.

In one embodiment, the working electrode 102' and the reference electrode 102" of the first electrode set 102 may have a spacer in a range of 0.01 mm to 5 mm, for example, 0.01 mm to 1 mm or 0.05 mm to 5 mm. The working electrode 102' and the reference electrode 102" of the first electrode set 102 may have an area ratio between 1 and 1.5, for example, between 1 and 1.2. By setting the above parameters, a stable response signal can be obtained when applying a voltage to the first electrode set 102 by the square wave voltammetry.

In one embodiment, the reaction reagent layer 106 may be disposed on the second reaction area 105 of the second electrode set 104. However, it should be noted that although FIG. 1 only illustrates the exemplary example that the reaction reagent layer 106 is disposed on the second reaction area 105 of the second electrode set 104, the reaction reagent layer 106 may also optionally extend to the first reaction area 103 of the first electrode set 102 in other embodiments according to different electrode materials, patterns, and arrangements of the provided test strip. The reaction reagent layer 106 may include a reaction enzyme and an electrical mediator. In one embodiment, the reaction reagent layer 106 merely includes one kind of reaction enzyme.

It should be realized that the aforementioned arrangement and schematic diagram of the test strip is merely one of the embodiments of the present disclosure. The present disclosure is not limited thereto. Various modifications and variations can be made to the disclosed embodiments according to the teaching of the present disclosure and the prior art by those skilled in the art.

Figure 2:
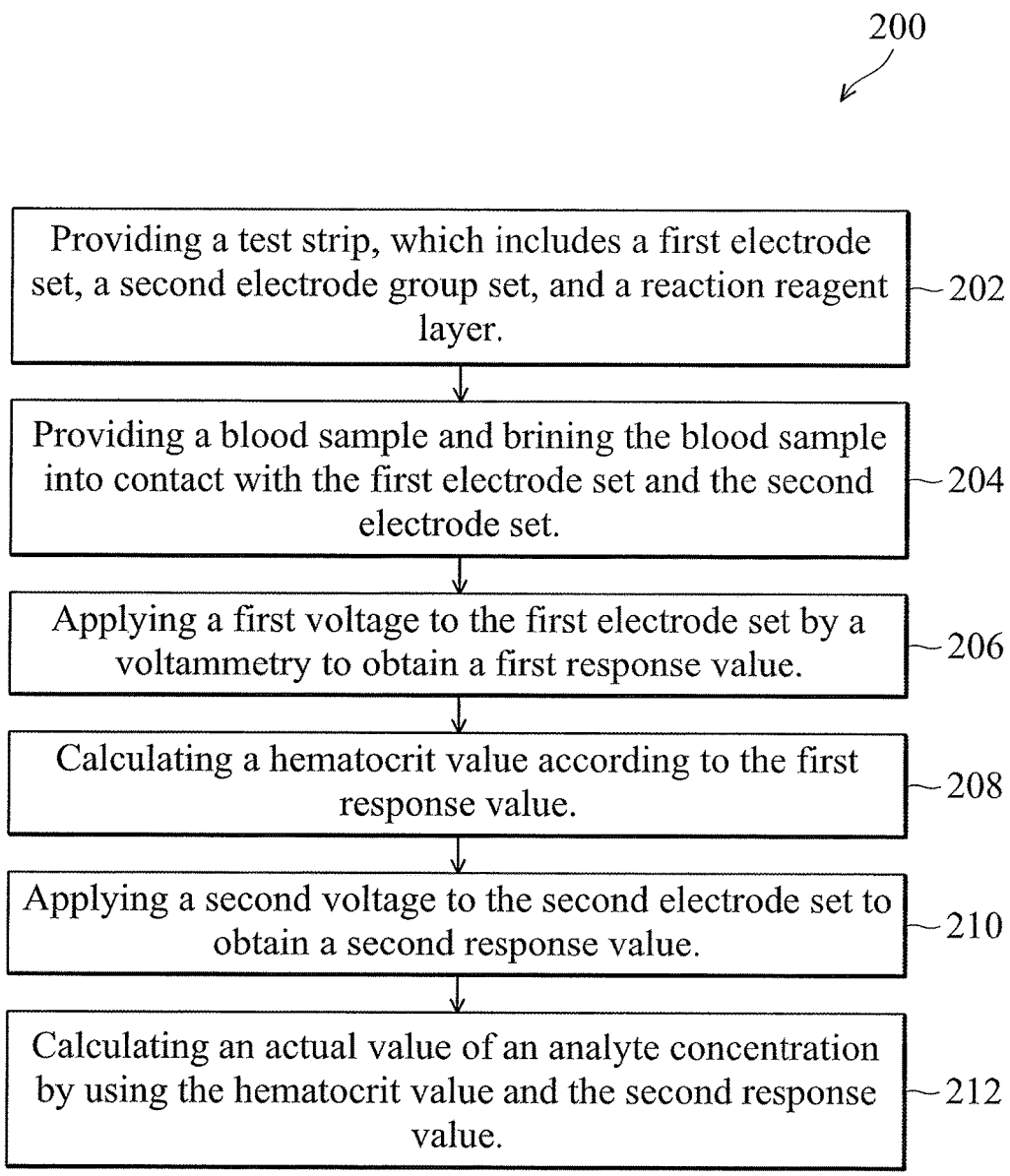
FIG. 2 illustrates a flow chart of the method for detecting the analyte concentration according to a first embodiment of the present disclosure.

According to first embodiments, the present disclosure provides a method 200 for detecting the analyte concentration, as shown in FIG. 2. FIG. 2 illustrates a flow chart of the method 200 for detecting the analyte concentration according to an embodiment of the present disclosure. The method 200 first proceeds to step 202 by providing a test strip. The test strip herein is substantially same as the test strip 100 shown in FIG. 1, which includes a first electrode set 102 having a first reaction area, a second electrode set 104 having a second reaction area, and a reaction reagent layer 106 disposed on the second reaction area 104. Similarly, the structure of the test strip herein may also include different variations, as the description of the test strip 100 of FIG. 1, and hence is not discussed again to avoid unnecessary repetition for the purpose of simplicity.

Next, the method 200 proceeds to step 204 by providing a blood sample and bringing the blood sample into contact with the first electrode set and the second electrode set of the test strip. In coordinate with the schematic diagram of the test strip 100 shown in FIG. 1, the first electrode set 102 may be disposed at the end relatively proximal to the sample inlet 108, and the second electrode set 104 may be disposed at the end relatively distal to the sample inlet 108. After the blood sample is introduced into the test strip from the sample inlet, it passes the first reaction area 103 and comes into contact with the first electrode set 102, and then it passes the second reaction area 105 and comes into contact with the second electrode set 104. The second electrode set 104 may optionally be used to detect the entrance of the sample. As such, the function of detection can be started when the sample is enough, so a more precise detection can be achieved.

Figure 3:
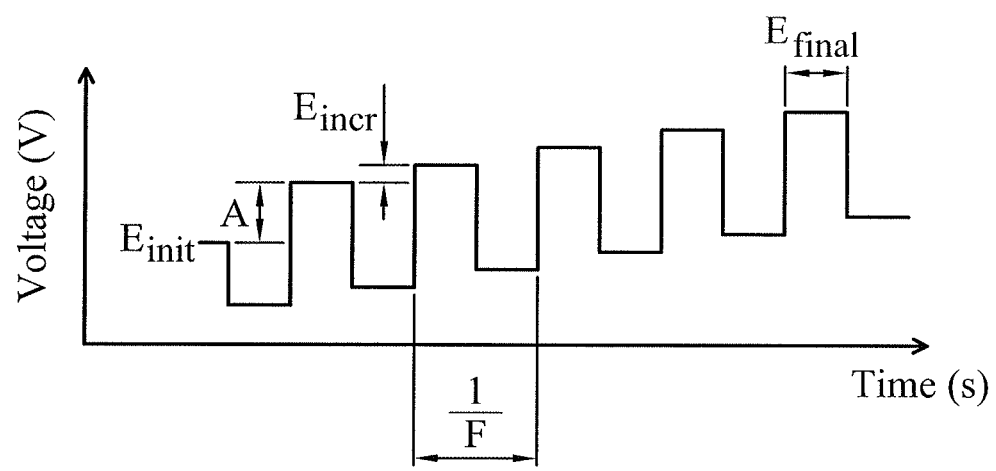
FIG. 3 illustrates a voltage type applied by the square wave voltammetry (SWV) according to an embodiment of the present disclosure.

The method 200 proceeds to step 206 by applying a first voltage to the first electrode set by voltammetry to obtain a first response value. In one embodiment, the adopted voltammetry is square wave voltammetry (SWV). The first voltage applied to the first electrode set by the square wave voltammetry (SWV) is a series of square wave-shaped voltages, as shown in FIG. 3. The square wave-shaped voltage is a positive voltage, whose initial voltage ($E_{init}$) gradually increases with time and reaches the final target voltage ($E_{final}$) by an increment voltage ($E_{incr}$). More specifically, the square wave-shaped voltage provides an oscillation between positive and negative voltage with constant voltage amplitude to the initial voltage ($E_{init}$), which is being a center of the oscillation. Then, a constant increment voltage ($E_{incr}$) is added and a new voltage ($E_{init}+E_{incr}$) functions as the center of the oscillation, which has a constant voltage amplitude, until the final target voltage ($E_{final}$) is reached. When modulated by providing appropriate parameters such as amplitude (A), frequency (F), and increment voltage ($E_{incr}$), the response value produced by blood samples with various different hematocrit values can be stably measured. In one embodiment, the first voltage may have constant amplitude, frequency, and increment voltage. For example, the frequency of the first voltage may be more than or equal to 100 Hz, for example, between 100 Hz and 4000 Hz. The amplitude of the first voltage may be more than or equal to 0.01 V, for example, between 0.01 V and 0.4 V. In one embodiment, the increment voltage of the first voltage may be between 0.01 V and 0.4 V, for example, between 0.05 V and 0.2 V. The voltage scan range of the first voltage may be between 0 V and 0.8 V, for example, between 0 V and 0.5 V. Also, the applying time of the first voltage may be between 0.01 seconds and 4 seconds, for example, between 0.01 seconds and 2 seconds.

However, it is worth mentioning that the first voltage applied to the first electrode set may be adaptively adjusted with the change of the condition of electrode material, pattern, arrangement, etc. For example, according to an embodiment of the present disclosure, when the electrode is formed of carbon ink, for example, screen printing electrodes (screen printed carbon electrode; SPCE), the frequency of the first voltage may be between 100 Hz and 500 Hz, for example, and the amplitude of the first voltage may be between 0.01 V and 0.4 V, for example. Also, in such case, the voltage scan range of the first voltage may be between 0 V and 0.5 V, for example, and the applying time of the first voltage may be between 0.01 seconds and 2 seconds, for example. According to another embodiment of the present disclosure, for example, when the electrode is formed of gold (Au), the frequency of the first voltage may be between 500 Hz and 4000 Hz, for example, and the amplitude of the first voltage may be between 0.1 V and 0.4 V, for example. Also, in such case, the voltage scan range of the first voltage may be between 0 V and 0.5 V, for example, and the applying time of the first voltage may be between 0.01 seconds and 2 seconds, for example.

It should be noted that the reason for specifically using the square wave voltammetry (SWV) to apply the first voltage to the first electrode set is because that the response value obtained from this method is stable and related with the hematocrit (Hct) value but not related with the blood glucose concentration. In one embodiment, the response value may be a current value, for example. However, as those skilled in the art will realize, the method for detecting the response values may include other variations. For example, when different circuit mechanism design is used, the current may be converted to voltage, capacitor, or other electrical form to conduct the test. The present disclosure is not limited thereto.

The method 200 proceeds to step 208 by calculating a hematocrit value according to the first response value. The corresponding hematocrit value can be obtained by using the relationship equation of the first response value and the hematocrit value or by using the reference table.

The method 200 proceeds to step 210 by applying a second voltage to the second electrode set to obtain a second response value. In step 210, the second voltage may be applied to the second electrode set by any appropriate method, such as amperometry, coulometry, potentiometry, voltammetry, impedance, or a combination thereof. However, the present disclosure is not limited thereto.

It should be noted that the sequence of applying the first voltage and the second voltage to the first electrode set and the second electrode set is not specifically limited. In the first embodiment of the present disclosure, as long as the first response value and the second response value can be obtained and the method for applying the first voltage is through voltammetry, any sequence can be performed in the present disclosure to obtain the final actual value of the calibrated blood glucose concentration. For example, in one embodiment, the first voltage may be applied to the first electrode set first, and the second voltage may be applied to the second electrode set later. In another embodiment, the second voltage may be applied to the second electrode set first, and the first voltage may be applied to the first electrode set later. Alternatively, in still another embodiment, the first voltage and the second voltage may be respectively applied to the first electrode set and the second electrode set in the meantime.

The method proceeds to step 212 by calculating the actual value of the analyte concentration by using the hematocrit value and the second response value. In one embodiment, the method for calculating the actual value of the analyte concentration by using the hematocrit value and the second response value may include using a compensation method or a reference table. But, it is not limited thereto. In another embodiment, the compensation method is to calculate a measured value of the analyte concentration according to the second response value. By using a relationship equation of the second response value and the analyte concentration or using a reference table, the corresponding measured value may be obtained. Then, a certain proportion of compensation is conducted according to the difference between the hematocrit value and the standard hematocrit value to obtain the actual value of the analyte concentration. In still another embodiment, the method of using a reference table is to obtain a linear equation related with the analyte concentration according to the hematocrit value. Then, the second response value is taken into the corresponding linear equation to obtain the actual value of the analyte concentration.

Figure 4:
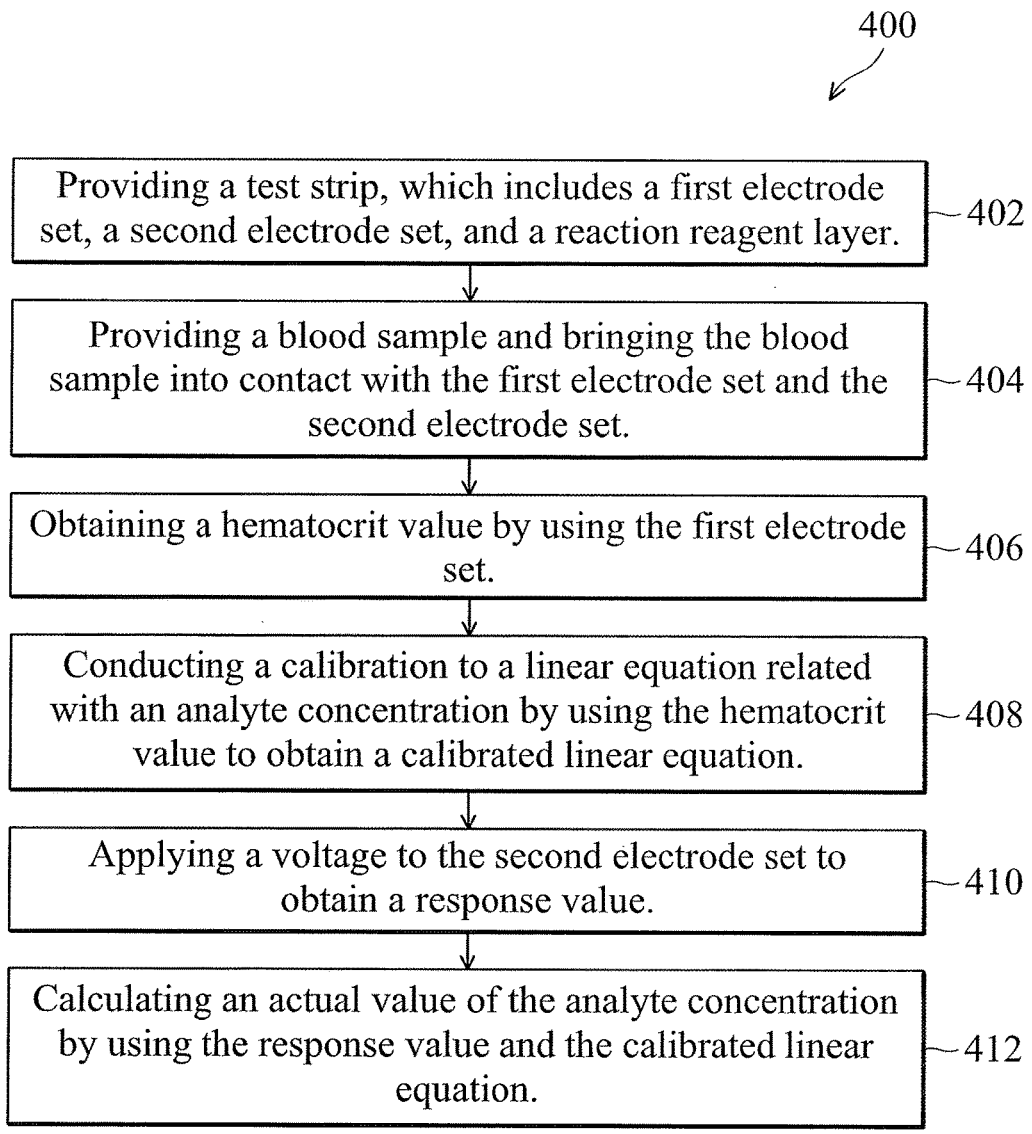
FIG. 4 illustrates a flow chart of the method for detecting the analyte concentration according to a second embodiment of the present disclosure.

According to second embodiments of the present disclosure, the present disclosure provides a method 400 for detecting the analyte concentration. FIG. 4 illustrates a flow chart of the method 400 for detecting the analyte concentration according to an embodiment of the present disclosure. The method 400 first proceeds to step 402 by providing a test strip. The test strip herein is substantially same as the test strip 100 shown in FIG. 1, which includes a first electrode set 102 having a first reaction area, a second electrode set 104 having a second reaction area, and a reaction reagent layer 106 disposed on the second reaction area 104. Similarly, the structure of the test strip herein may also include different variations, as the description of the test strip 100 of FIG. 1, and hence is not discussed again to avoid unnecessary repetition for the purpose of simplicity.

Next, the method 400 proceeds to step 404 by providing a blood sample and bringing the blood sample into contact with the first electrode set and the second electrode set. In coordinate with the schematic diagram of the test strip 100 shown in FIG. 1, the first electrode set 102 may be disposed at the end relatively proximal to the sample inlet 108, and the second electrode set 104 may be disposed at the end relatively distal to the sample inlet 108. After the sample is introduced into the test strip from the sample inlet, it passes the first reaction area 103 and comes into contact with the first electrode set 102, and then it passes the second reaction area 105 and comes into contact with the second electrode set 104. The second electrode set 104 may optionally be used to detect the entrance of the sample. As such, the function of detection can be started when the sample is enough, so a more precise detection can be achieved.

The method 400 proceeds to step 406 by obtaining a hematocrit value by using the first electrode set 102. In this step, the measurement of the hematocrit value is not limited to using voltammetry, for example, and may include the use of amperometry, coulometry, potentiometry, voltammetry, impedance, or a combination thereof. However, the present disclosure is not limited thereto.

The method 400 proceeds to step 408 by conducting a calibration to a linear equation related with the analyte concentration by using the hematocrit value to obtain a calibrated linear equation. The linear equation related with the analyte concentration is y=ax+b, wherein it is a conversion equation of the response value obtained by the method of step 406 (for example, a response current value) and the analyte concentration when the hematocrit value of the blood is 0%. In this equation, y is the response value (for example, a response current value), a is a slope parameter, x is the analyte concentration, b is an interception parameter. Biases are easily produced during the detection of hematocrit value due to different detection method or detectors. If the blood with 0% hematocrit value (i.e. the plasma) is used as a base to obtain the linear equation related with the analyte concentration, the effect of the detection bias may be eliminated. In another embodiment, the blood with a standard hematocrit value (for example, a hematocrit value of 40% to 45%) may also be used as a base to obtain the linear equation related with the analyte concentration. It is worth noting that the present disclosure merely needs to provide a preset linear equation, such as the linear equation related with the analyte concentration obtained by using the blood with a hematocrit value of 0% or 40% to 45% as a base, and then conduct a calibrate to the linear equation by using the obtained hematocrit value, a calibrated linear equation corresponding to the obtained hematocrit value can be directly obtained.

In one embodiment, the method for conducting a calibration to the linear equation related with the analyte concentration by using the hematocrit value to obtain the calibrated linear equation includes: obtaining a slope coefficient and an interception coefficient corresponding to the hematocrit value according to a reference table or a relationship equation, and conducting a calibration to the linear equation related with the analyte concentration by using the slope coefficient and the interception coefficient to obtain the calibrated linear equation. In another embodiment, the reference table includes the slope coefficients and the interception coefficients corresponding to a plurality of hematocrit values. These hematocrit values may be in a range of 10% to 70%. For example, the hematocrit values may include 20%, 30%, 35%, 43%, 55%, 60%, 65%, or 70%. It should be noted that, the slope coefficient and the interception coefficient of different hematocrit values can be calculated by using the interpolation method. Therefore, it is not limited to the above specific values. In still another embodiment, the relationship equation may include a constant, a polynomial, or a linear equation. A corresponding slope coefficient or interception coefficient can be obtained by taking the hematocrit value into this relationship equation.

The method 400 proceeds to step 410 by applying a voltage to the second electrode set to obtain a response value. In step 412, the voltage may be applied to the second electrode set by any appropriate method, such as amperometry, coulometry, potentiometry, voltammetry, impedance, or a combination thereof. However, the present disclosure is not limited thereto.

The method 400 proceeds to step 412 by calculating the actual value of the analyte concentration by using the response value and the calibrated linear equation. The analyte concentration may be a concentration of blood glucose. The described calibrated linear equation is y=a'x+b', wherein y is the response value, a' is a slope parameter calibrated by the slope coefficient, x is the actual value of the analyte concentration, b' is an interception parameter calibrated by the interception coefficient.

In addition, the present disclosure may further include a third embodiment. The flow of the method for detecting the analyte concentration is substantially same as the second embodiment of the present disclosure, while the step 406 is replaced by applying a first voltage to the first electrode set by voltammetry to obtain a first response value. Then, calculating a hematocrit value according to the first response value. For the purpose of simplicity, the following merely describes the different parts between the third embodiment and the second embodiment. The other same step can refer to the steps 402 to 404 and 408 to 412 of the second embodiment of the present disclosure, and hence is not discussed again to avoid unnecessary repetition for the purpose of simplicity.

In detail, in the third embodiment of the present disclosure, the step 406 of the second embodiment is replaced by applying a first voltage to the first electrode set by voltammetry to obtain a first response value. In one embodiment, the adopted voltammetry is the square wave voltammetry (SWV). The first voltage applied to the first electrode set by the square wave voltammetry (SWV) is a series of square wave-shaped voltages, as shown in FIG. 3. The square wave-shaped voltage is a positive voltage, whose initial voltage ($E_{init}$) gradually increases with time and reaches the final target voltage ($E_{final}$) by an increment voltage ($E_{incr}$). More specifically, the square wave-shaped voltage provides an oscillation between positive and negative voltage with constant voltage amplitude to the initial voltage ($E_{init}$), which is being a center. Then, a constant increment voltage ($E_{incr}$) is added and a new voltage ($E_{init}+E_{incr}$) functions as the center of the oscillation, which has a constant voltage amplitude, until the final target voltage ($E_{final}$) is reached. When modulated by providing appropriate parameters such as amplitude (A), frequency (F), and increment voltage ($E_{incr}$), the response value produced by blood samples with various different hematocrit values can be stably measured. In one embodiment, the first voltage may have constant amplitude, frequency, and increment voltage. For example, the frequency of the first voltage may be more than or equal to 100 Hz, for example, between 100 Hz and 4000 Hz. The amplitude of the first voltage is more than or equal to 0.01 V, for example, between 0.01 V and 0.4 V. In one embodiment, the increment voltage of the first voltage may be between 0.01 V and 0.4 V, for example, between 0.05 V and 0.2 V. The voltage scan range of the first voltage may be between 0 V and 0.8 V, for example, between 0 V and 0.5 V. Also, the applying time of the first voltage may be between 0.01 seconds and 4 seconds, for example, between 0.01 seconds and 2 seconds.

Next, a hematocrit value is calculated according to the first response value. The present inventors find that the relationship of the first response value (current) is inversely proportional to the hematocrit value, which can be represented as a relationship equation. The relationship equation may include a polynomial or a linear equation. Thereafter, a corresponding hematocrit value can be obtained after taking the detected first response value into the relationship equation. In one embodiment, the relationship of the first response value and the hematocrit value can be represented in a reference table. The range of hematocrit value in the reference table may be between 10% and 70%, for example, the hematocrit value may include 20%, 30%, 35%, 43%, 55%, 60%, 65%, or 70%. It should be noted that, according to the inverse relationship between the first response value and the hematocrit value, different hematocrit values can be calculated by using the interpolation method and are not limited to the above specific values.

In short, the method for detecting the analyte concentration provided by the first embodiment of the present disclosure uses voltammetry to detect a hematocrit value which is not affected by the analyte concentration. Then, the actual value of the analyte concentration is obtained according to the hematocrit value. In addition, the method for detecting the analyte concentration provided by the second embodiment of the present disclosure uses the detected hematocrit value to obtain the slope coefficient and the interception coefficient to calibrate the preset linear equation. Then, the actual value of the analyte concentration can be obtained directly by taking the response value related with the analyte concentration into the calibrated linear equation. In the embodiments of the second embodiment of the present disclosure, the method for using the first electrode set to obtain the hematocrit value may include amperometry, coulometry, potentiometry, voltammetry, impedance, or a combination thereof. In another embodiment of the second embodiment, the method for obtaining the hematocrit value includes converting the time of passing through the electrode pair or using an AC (alternating current) impedance method.

In addition, in the method for detecting the analyte concentration provided by the second embodiment of the present disclosure, if the hematocrit value which is not affected by the analyte concentration is also detected by voltammetry, it becomes the third embodiment of the present disclosure. In other words, the method for detecting the analyte concentration provided by the second embodiment of the present disclosure uses voltammetry to detect a hematocrit value which is not affected by the analyte concentration. Then, a calibrated linear equation is obtained by using the hematocrit value. The actual value of the analyte concentration can be obtained directly by taking the response value related with the analyte concentration into the calibrated linear equation.

The general method used to calibrate the bias of the analyte concentration produced by the effect of hematocrit value includes directly measuring the hematocrit value and calibrating and compensating the measured value. However, the measured value which is only related with the hematocrit value but not related with other factors such as glucose concentration, triacylglycerol concentration, etc. cannot be obtained by these methods. In addition, the measured value obtained by the blood glucose meter in the market so far usually can directly and precisely reflect the actual blood glucose concentration when the hematocrit value is in a range that the normal blood has (for example, 30% to 55%). Some blood glucose meters can only precisely conduct the test under specific hematocrit values (such as 42%). When the hematocrit value of the sample to be detected is not in a range wherein the blood glucose meter can precisely conduct the test, the hematocrit value of the sample has to be adjusted in advance, or a detection bias will be produced.

The present disclosure provides a method for detecting the analyte concentration. The detection bias of the analyte concentration that results from the hematocrit value can be correctly calibrated using this method. In addition, the method for detecting the analyte concentration provided by the present disclosure renders different hematocrit values to have associations between each other according to the calibration relationship or calculation method obtained by a deep research of the present inventors. Furthermore, the blood glucose concentration can be correctly measured while the hematocrit value is in a range of 10% to 70%, which conforms to the examination standard draft by Food and Drug Administration (FDA) for the blood glucose meter to be listed.

In addition, the square wave voltammetry (SWV) used in the present disclosure is easier to be constructed on the detector, and the cost is lower. Moreover, the sensitivity of the square wave voltammetry (SWV) to the blood glucose concentration is far lower than other general methods used to detect the hematocrit (Hct) value in the market. Therefore, an actual blood glucose concentration can be calculated more correctly.

The following examples are provided to illustrate the method for measuring the analyte concentration provided by the present disclosure.

EXAMPLE 1

Provide Test Strip and Blood Sample

First, a test strip was provided. The test strip includes two electrode sets formed of the screen printed carbon ink. The two electrode sets respectively have a working electrode and a reference electrode. Next, the glucose oxidase, potassium ferricyanide, PBS buffer, and bovine serum albumin were used as reaction reagent layer and covered on the second electrode set. No reaction reagent layer was covered on the first electrode set. The reference electrode of the second electrode set was used to detect the entrance of the sample and determine if the sample is enough. Five kinds of samples with different blood glucose concentrations (57 mg/dl, 75.6 mg/dl, 140 mg/dl, 203 mg/dl, 327 mg/dl) were used and were respectively prepared to have nine different hematocrit values (0%, 20%, 30%, 35%, 43%, 55%, 60%, 65%, 70%) as the blood sample, then were introduced through the sample inlet. Samples passed through the first electrode set first, and then reached the second electrode set. The function of measurement was started when the entrance of the sample was detected by the reference electrode of the second electrode set.

EXAMPLE 2

Sample Response Current Value Measured by Applying Voltage Through the Square Wave Voltammetry (SWV)

Figure 5:
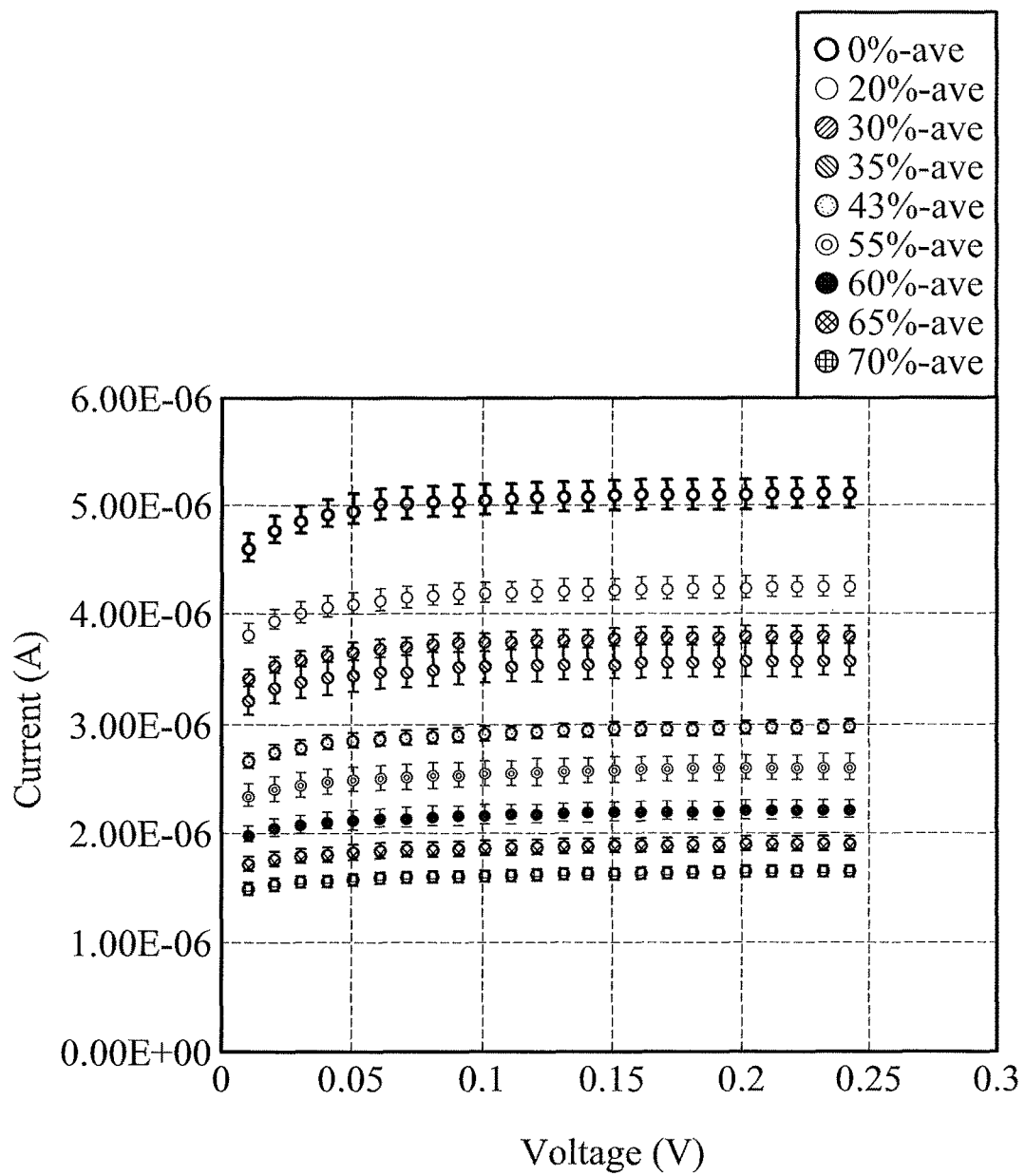
FIG. 5 illustrates a diagram of the average current of samples with the same hematocrit value but different blood glucose concentrations.

After the measurement function was started, a series of square wave-shaped voltages were applied to the first electrode set by the square wave voltammetry (SWV) to modulate the amplitude into 0.01 V, the frequency into 100 Hz, the increment voltage into 0.01 V. The voltage scan range was between 0 V and 0.5 V. Then, the response current produced by various samples were measured. The result was shown in FIG. 5. A voltage of 0.24 V was used to calculate the bias of the response current of different blood glucose concentrations. The resultant coefficient variance of 0% Hct was 2.68%, the resultant coefficient variance of 20% Hct was 2.24%, the resultant coefficient variance of 30% Hct was 2.03%, the resultant coefficient variance of 35% Hct was 4.23%, the resultant coefficient variance of 43% Hct was 2.17%, the resultant coefficient variance of 55% Hct was 4.5%, the resultant coefficient variance of 60% Hct was 4.01%, the resultant coefficient variance of 65% Hct was 3.61%, and the resultant coefficient variance of 70% Hct was 2.68%. It can be observed from FIG. 5 that the samples with lower hematocrit values produce higher currents, while the samples with higher hematocrit values produce lower currents. At the same time, it can be found that although the blood glucose concentrations are different, the measured response currents were less affected by the blood glucose concentration (a coefficient variance less than 5%) or even not affected by the blood glucose concentration when the voltage was applied by square wave voltammetry.

EXAMPLE 3

Relationship of the Response Current and the Hematocrit Value

Figure 6:
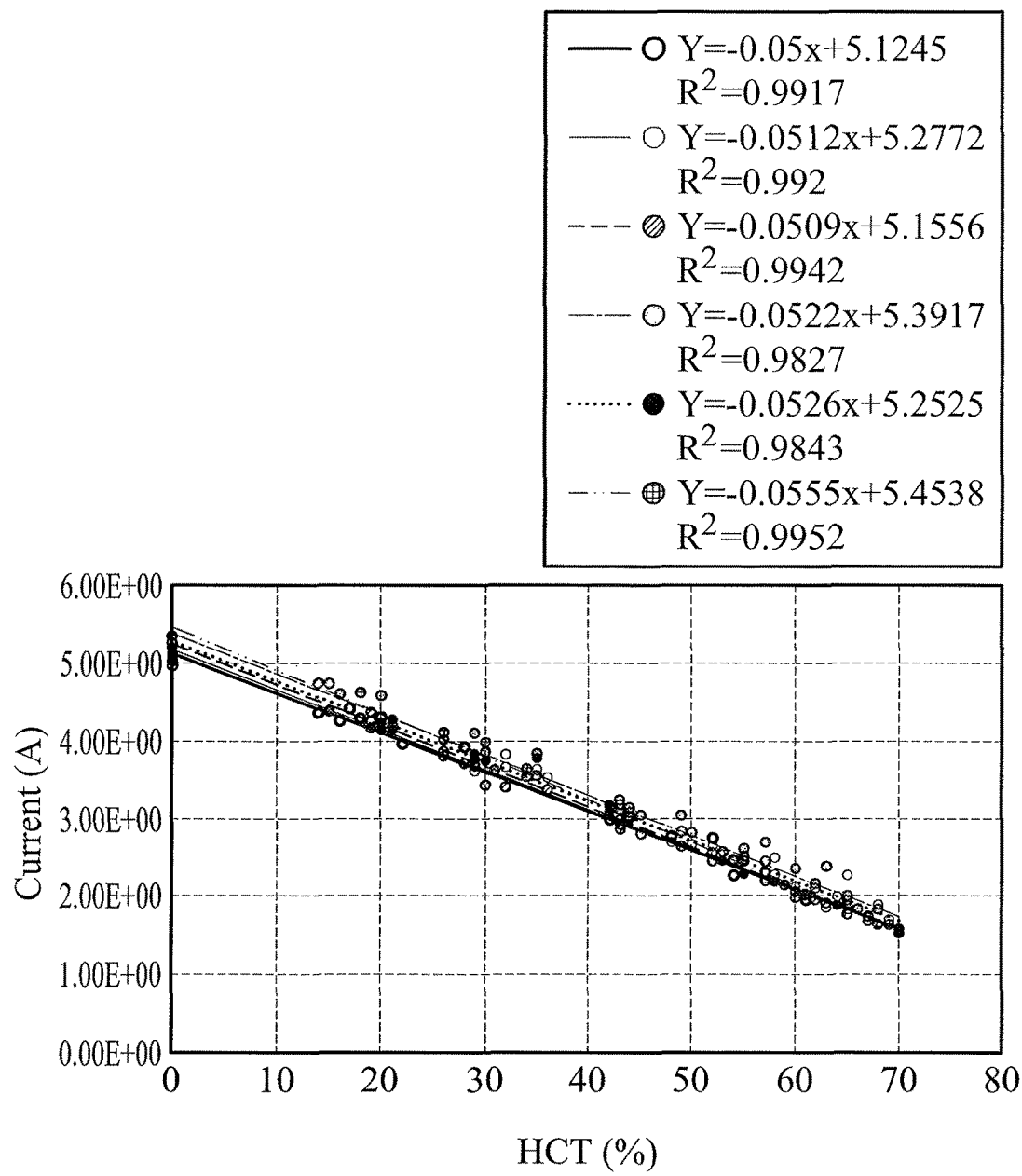
FIG. 6 illustrates the relationship between the response current value and the hematocrit values of the samples according to some embodiments of the present disclosure.

The experiments were repeatedly conducted by using venous blood from different individuals, which were prepared to have different hematocrit values and used as samples. Hematocrit values of various samples and the response current values were recorded. The relationship of the response current values and the hematocrit values were calculated according to the experimental results, as shown in FIG. 6. It can be found that the response current values were indeed inversely proportional to the hematocrit values. Therefore, after the samples were introduced into the test strip and the detection function was started, a response current could be obtained by applying a voltage though the square wave voltammetry (SWV) to estimate the corresponding hematocrit values.

EXAMPLE 4

Figure 7:
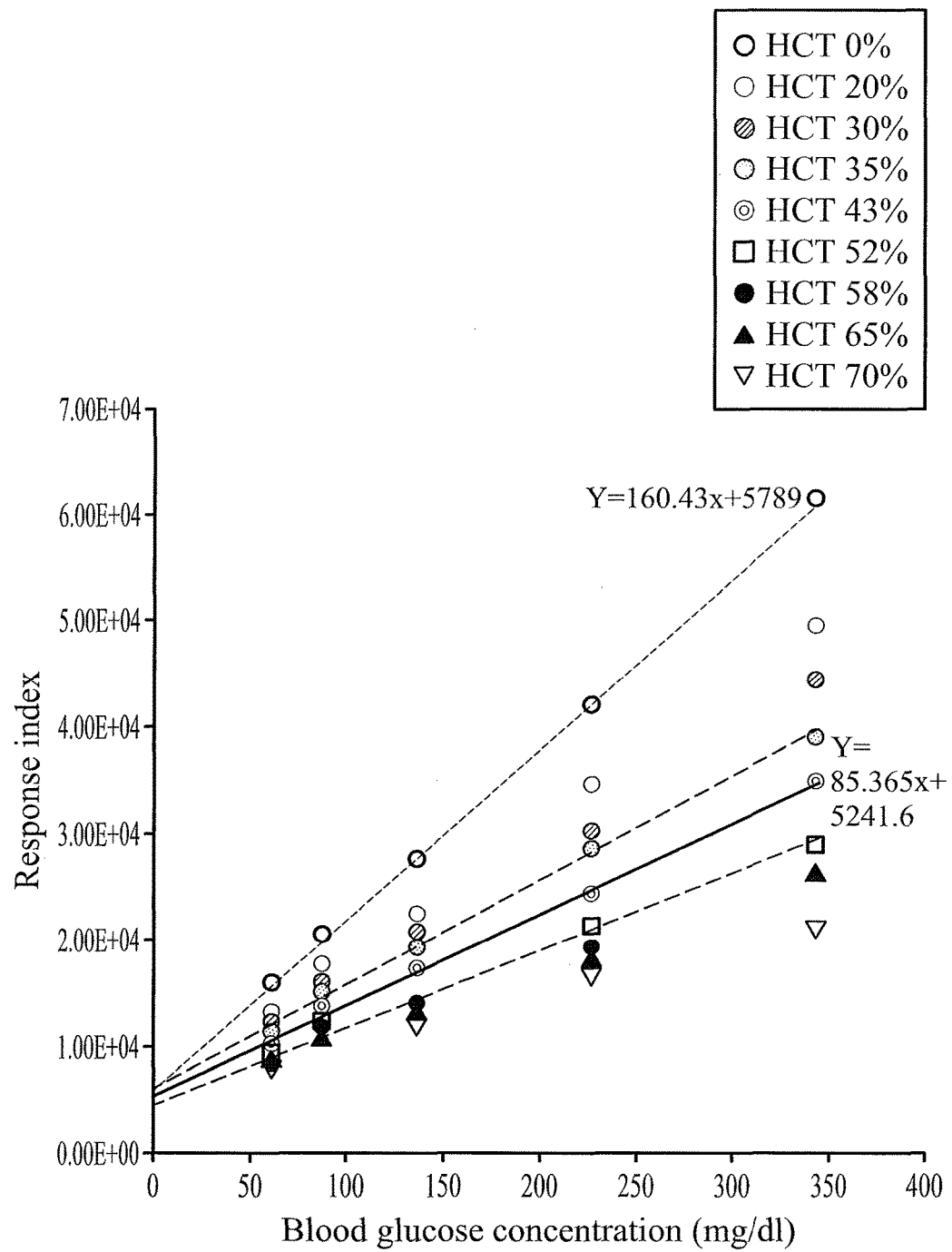
FIG. 7 illustrates the relationship between the detected current value related with the blood glucose concentrations and different hematocrit values of the samples according to some embodiments of the present disclosure.

Relationship of Different Hematocrit Values and the Response Current Values Related with the Blood Glucose Concentration After the different whole blood samples were introduced into the sample channel, a voltage of 0.3 V was applied to the second electrode set and the response current on the test strip was detected. If the whole blood samples with different blood glucose concentrations were used, the linear equation of the blood glucose concentration and the response currents could be obtained. At this time, if the whole blood samples with different hematocrit values were used to conduct the test, the linear equation of the blood glucose concentration and the response currents of the whole blood samples with different hematocrit values could be obtained. As shown in FIG. 7, if the hematocrit value of the sample is too high, it can easily cause an inferior dissolution of the reagent in the test strip. Moreover, since the reaction of reagent is affected by a slightly high oxygen concentration, the reaction enzyme produces a slightly lower response current value which is related with the blood glucose. Conversely, when the hematocrit value of the sample is too low, the response current value produced by the reaction enzyme is slightly higher. After observing the linear relationship of the blood glucose and the response current of samples with various hematocrit values, it can be further found that there is a constant relationship between the linear relationship of the blood glucose and the response current of various hematocrit values.

EXAMPLE 5

Deduce the Equation of Hct X %

If the different straight line $y=a_1x+b_1$ of Hct X % is compared to the different straight line $y=ax+b$ of Hct 0%, it can be found that the Ka value of $a/a_1$ is a close value in the blood samples with different blood glucose concentrations. Data of the Ka value as shown in Table 1 can be obtained if the slope of Hct 0% was used as a base to conduct a calculation toward other slopes of Hct X %.

TABLE 1

| Hct value | Ka value |
| --- | --- |
| 0% | 1 |
| 20% | 1.2 |
| 30% | 1.4 |
| 35% | 1.5 |
| 43% | 1.8 |
| 55% | 2.2 |
| 60% | 2.5 |
| 65% | 2.9 |
| 70% | 3.2 |

Figure 8A:
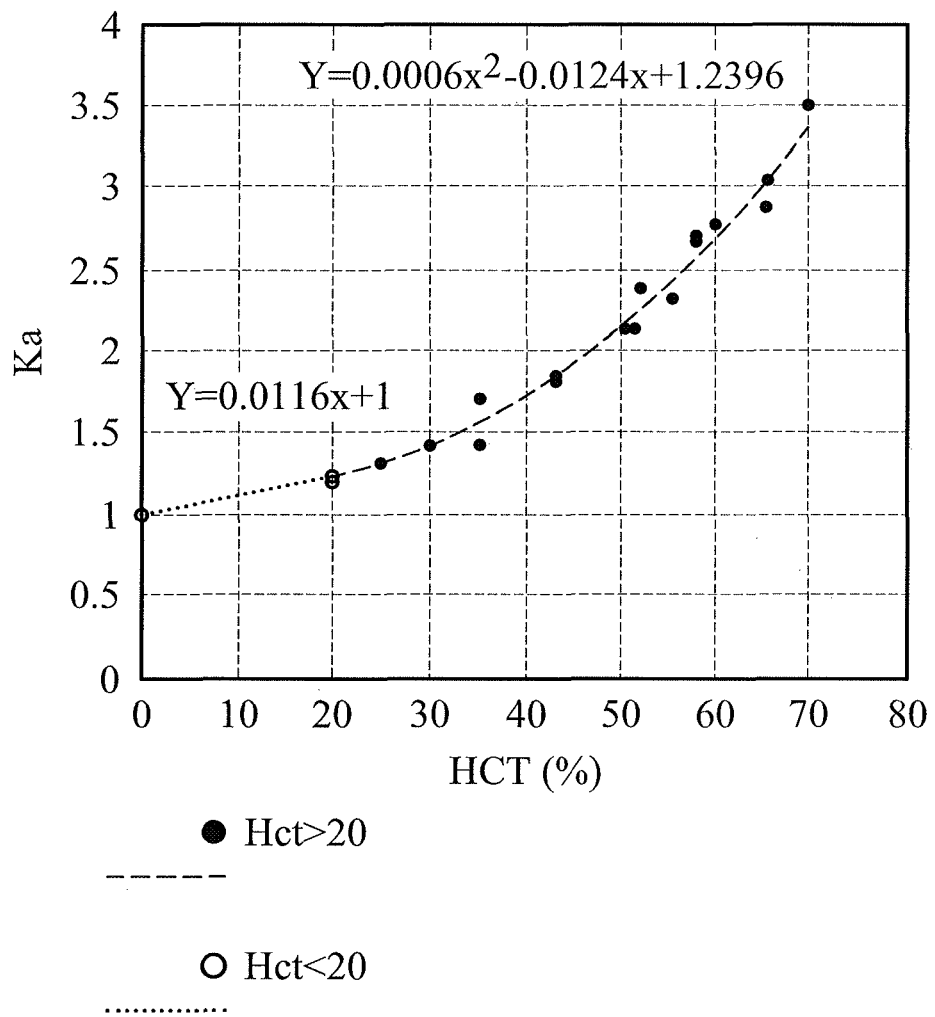
FIG. 8A illustrates the representative trend equation of the Ka value calculated according to some embodiments of the present disclosure.
Figure 8B:
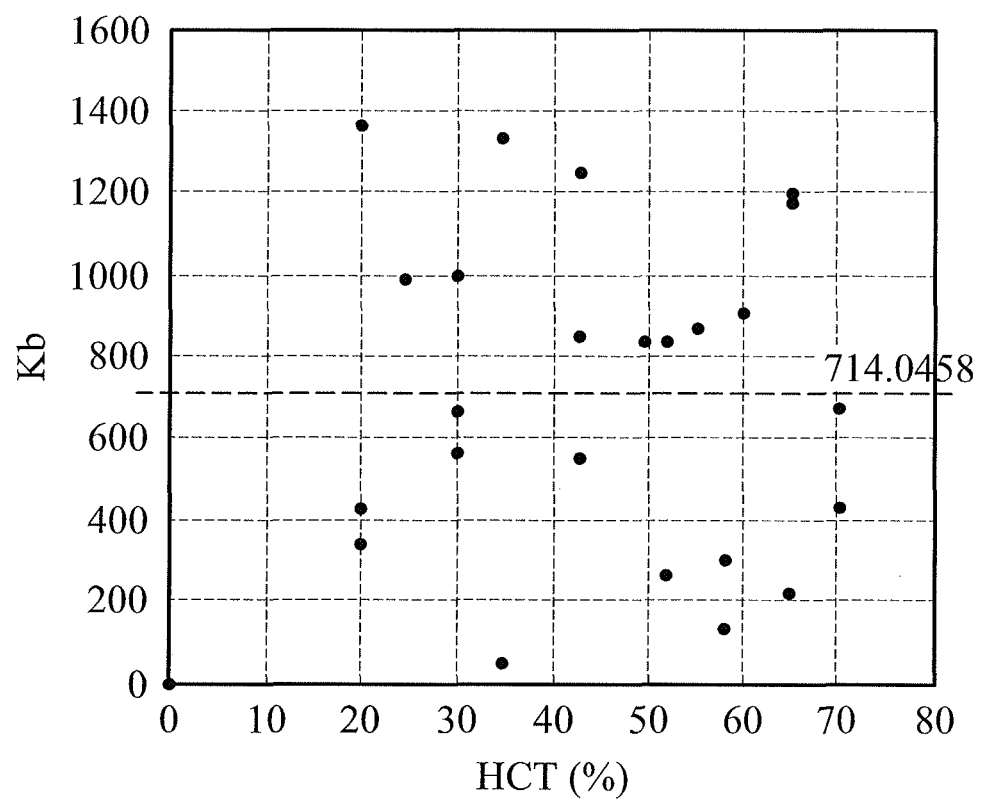
FIG. 8B illustrates the distribution range of the Kb value calculated according to some embodiments of the present disclosure.

After the slope ratio (represented as Ka) of various samples with different hematocrit values was compared to the hematocrit values, a trend of the Ka value can be obtained by induction, as shown in FIG. 8A. Also, the distribution range of the difference of the constant $b-b_1$ (represented as Kb) can be obtained by induction after comparing to the hematocrit values of various samples with different hematocrit values, as shown in FIG. 8B. From the above relationship of $a/a_1=Ka$ and $b-b_1=Kb$, it can be known that the straight line $y=a_1x+b_1$ of Hct X % can also be represented as the straight line $y=(a/Ka)x+(b-Kb)$.

Next, a large amount of data is used to calculate a representative trend equation of the Ka value, as shown in FIG. 8A. When the Hct value >20, the representative trend equation of the Ka value is $y=0.0006x^2-0.0124x+1.2396$. When the Hct value <20, the representative trend equation of the Ka value is $y=0.0116x+1$. In addition, as can be seen from FIG. 8B, since the Kb value is a random number, the difference between the Kb values is not great. Therefore, an average value of 714 is used to represent the constant of the Kb value in the following relationship equation.

After the hematocrit value was estimated by the method of Example 3, the value was taken into the representative trend equation $y=0.0006x^2-0.0124x+1.2396$ of the Ka value to calculate the Ka value. As shown in FIG. 2, it can be observed that the same hematocrit value has a constant range of the Ka value, which is not affected by different blood glucose concentrations. Next, the equation of Hct X % conforming to the relationship of the corresponding slope and interception could be deduced after the obtained Ka and Kb were taken into the straight line $y=(a/Ka)x+(b-Kb)$. When Hct is 0%, the deduced equation of Hct 0% is y=160.43 x+5789, wherein x represents the detected current related with the blood glucose, and y represents the corresponding blood glucose concentration. Therefore, after the equation of Hct X % conforming to the relationship of the corresponding slope and interception of various hematocrit values was deduced, the corresponding blood glucose concentration could be deduced correctly as long as the detected current related with the blood glucose is provided. The Ka value and the Kb value of the present disclosure only relate with the hematocrit value and do not change with different blood glucose concentrations or different samples; therefore, only one preset linear equation is needed for the present disclosure to directly obtain the calibrated linear equation which is corresponding to different hematocrit values by conducting a calibration to the preset linear equation by using the Ka value and the Kb value deduced from different hematocrit values.

TABLE 2

| Ka value | 57 mg/dl | 75.6 mg/dl | 140 mg/dl | 203 mg/dl | 327 mg/dl |
|---|---|---|---|---|---|
| HCT 0% | 1 | 1 | 1 | 1 | 1 |
| HCT 20% | 1.2206 | 1.2206 | 1.2316 | 1.2316 | 1.2206 |
| HCT 30% | 1.4076 | 1.3228 | 1.3628 | 1.3846 | 1.3228 |
| HCT 35% | 1.4572 | 1.4318 | 1.5708 | 1.4572 | 1.4318 |
| HCT 43% | 1.8158 | 1.8158 | 1.8158 | 1.8158 | 1.8158 |
| HCT 55% | 2.2172 | 2.0726 | 2.3726 | 2.2172 | 2.0268 |
| HCT 60% | 2.4822 | 2.4822 | 2.6556 | 2.5966 | 2.5966 |
| HCT 65% | 2.9036 | 2.7772 | 2.9686 | 2.9686 | 2.8398 |
| HCT 70% | 3.2406 | 3.3116 | 3.1022 | 3.3116 | 3.2406 |

EXAMPLE 6

Figure 9A:
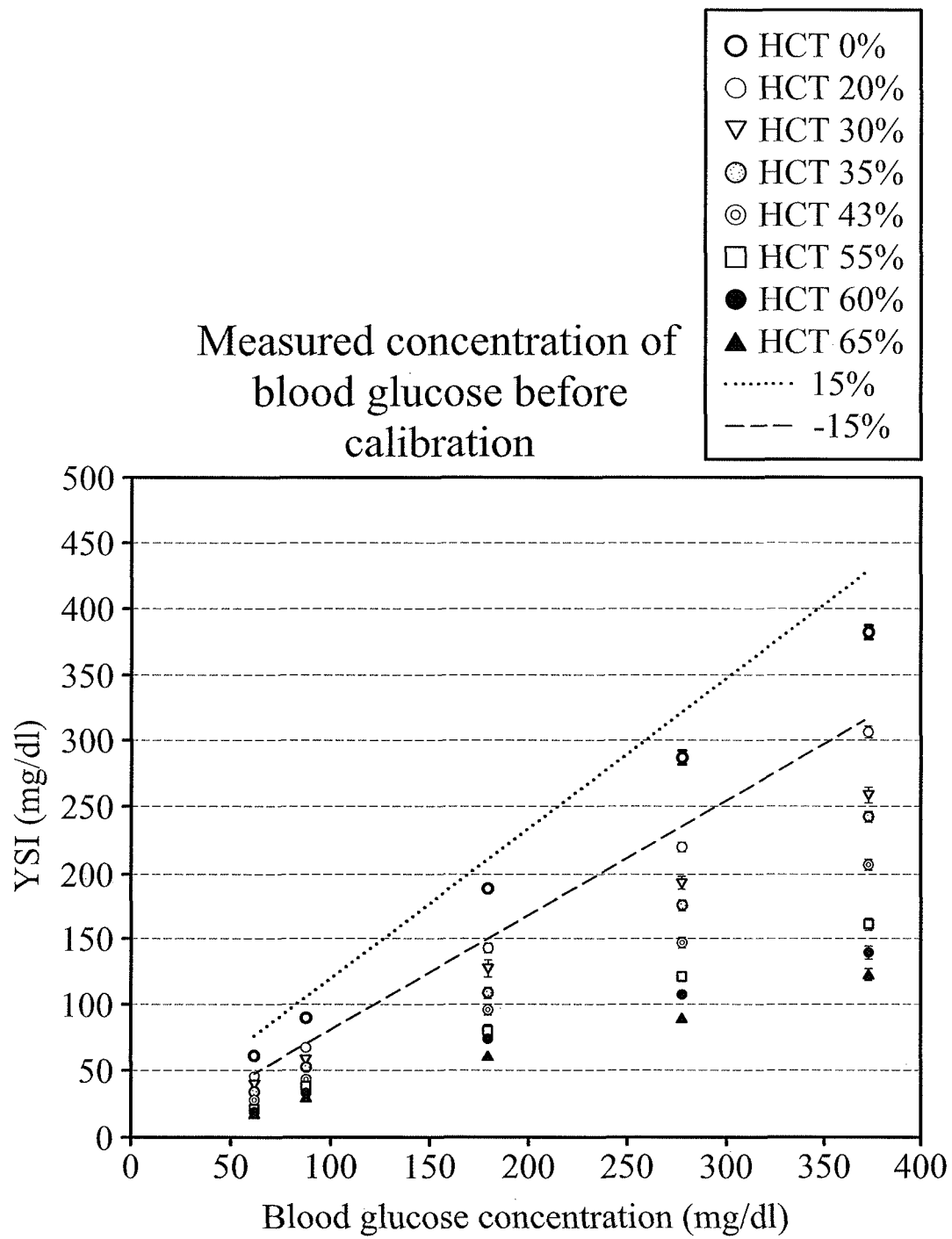
FIGS. 9A and 9B respectively illustrates the comparison of the measured blood glucose concentration before and after the calibration according to some embodiments of the present disclosure.
Figure 9B:
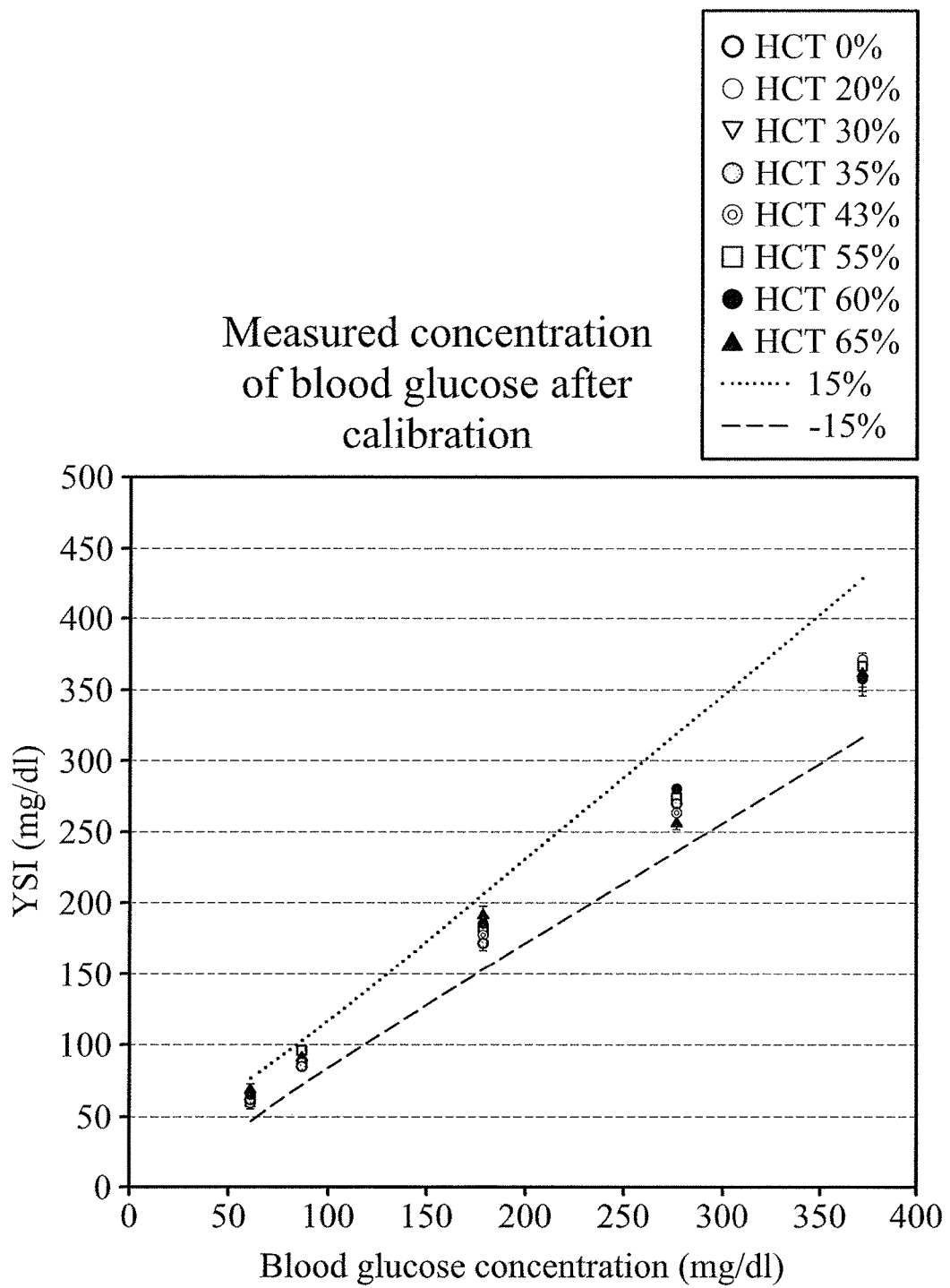

Comparison of the Measured Blood Glucose Concentration Before and after the Calibration The five samples with different blood glucose concentrations (57 mg/dl, 75.6 mg/dl, 140 mg/dl, 203 mg/dl, 327 mg/dl) of Example 1 were used and respectively prepared to have eight different hematocrit values (0%, 20%, 30%, 35%, 43%, 55%, 60%, 65%), which were measured thereafter. The measured blood glucose concentrations without calibration were shown in FIG. 9A. As can be seen from FIG. 9A, various biases of the measured values were produced at the same blood glucose concentration since the interference of various hematocrit values. In comparison, though the methods of Examples 1 to 5, the original interferences of the hematocrit values have been eliminated after the measured blood glucose concentration were calibrated. The data of samples became more concentrated at the same blood glucose concentration, as shown in FIG. 9B.

As proven by the above results, the present disclosure successfully uses the square wave voltammetry (SWV) to detect and estimate the hematocrit values, and uses the hematocrit values to deduce the equation of Hct X % conforming to the corresponding slope and interception from the equation of Hct 0%. In the hematocrit range of 20% to 65%, the actual value of the analyte concentration can be correctly estimated by directly using the detected current related with the analyte concentration. Regarding the bias of the measured blood glucose concentration and the standard values, is reduced to ±15% after the calibration, compared to the bias of 0% to 80% before the calibration.

While the disclosure has been described by way of example and in terms of the embodiments, it is to be understood that the disclosure is not limited to the disclosed embodiments. It will be apparent to those skilled in the art that various modifications and variations can be made to the disclosed embodiments. Therefore, the true scope of the disclosure is indicated by the following claims and their equivalents.

What is claimed is:

1. A method for detecting an analyte concentration, the method comprising:
   providing a test strip comprising:
      a first electrode set comprising a first reaction area;
      a second electrode set comprising a second reaction area; and
      a reaction reagent layer disposed on the second reaction area;
   providing a blood sample and bringing the blood sample into contact with the first electrode set and the second electrode set;
   applying a first voltage to the first electrode set by a square wave voltammetry (SWV) to obtain a first response value;
   calculating a hematocrit value according to the first response value;
   applying a second voltage to the second electrode set to obtain a second response value; and
   calculating an actual value of the analyte concentration by using the hematocrit value and the second response value.

2. The method for detecting the analyte concentration as claimed in claim 1, wherein the reaction reagent layer comprises a reaction enzyme and an electrical medium.

3. The method for detecting the analyte concentration as claimed in claim 1, wherein the first electrode set and the second electrode set respectively comprises a working electrode and a reference electrode.

4. The method for detecting the analyte concentration as claimed in claim 1, wherein the first electrode set comprises a working electrode and a reference electrode, the working electrode and the reference electrode of the first electrode set has a spacer in a range of 0.01 mm to 5 mm and/or the working electrode and the reference electrode of the first electrode set has an area ratio between 1 and 1.5.

5. The method for detecting the analyte concentration as claimed in claim 1, wherein a frequency of the first voltage is more than or equals to 100 Hz, an amplitude of the first voltage is more than or equals to 0.01 V, and/or an increment voltage of the first voltage is between 0.01 V and 0.4 V.

6. The method for detecting the analyte concentration as claimed in claim 1, wherein a voltage scan range of the first voltage is between 0 V and 0.8 V and/or the applying time of the first voltage is between 0.01 seconds and 4 seconds.

7. The method for detecting the analyte concentration as claimed in claim 1, further comprising:
   conducting a calibration to a linear equation related to the analyte concentration by using the hematocrit value to obtain a calibrated linear equation; and
   calculating an actual value of the analyte concentration according to the second response value and the calibrated linear equation.

8. The method for detecting the analyte concentration as claimed in claim 7, wherein the method for conducting the calibration to the linear equation related to the analyte concentration by using the hematocrit value to obtain the calibrated linear equation comprises:
   obtaining a slope coefficient and an interception coefficient corresponding to the hematocrit value according to a reference table or a relationship equation; and conducting a calibration to the linear equation related to the analyte concentration by using the slope coefficient and the interception coefficient to obtain the calibrated linear equation.

9. The method for detecting the analyte concentration as claimed in claim 8, wherein the reference table comprises the slope coefficients and the interception coefficients corresponding to a plurality of hematocrit values, wherein the hematocrit values are in a range of 10% to 70%.

10. The method for detecting the analyte concentration as claimed in claim 7, wherein the linear equation related to the analyte concentration is y=ax+b, wherein y is the second response value, a is a slope parameter, x is the analyte concentration, and b is an interception parameter, wherein the linear equation y=ax+b is a conversion equation of the second response value and the analyte concentration when the hematocrit value of the blood sample is 0%.

11. The method for detecting the analyte concentration as claimed in claim 7, wherein the linear equation related to the analyte concentration is y=ax+b, wherein y is the second response value, a is a slope parameter, x is the analyte concentration, and b is an interception parameter, wherein the linear equation y=ax+b is a conversion equation of the second response value and the analyte concentration when the hematocrit value of the blood sample is 40% to 45%.

12. The method for detecting the analyte concentration as claimed in claim 8, wherein the calibrated linear equation is y=a'x+b', wherein y is the second response value, a' is a slope parameter calibrated by the slope coefficient, x is the actual value of the analyte concentration, b' is an interception parameter calibrated by the interception coefficient.

13. A method for detecting an analyte concentration, comprising:
  providing a test strip comprising:
    a first electrode set comprising a first reaction area;
    a second electrode set comprising a second reaction area; and
    a reaction reagent layer disposed on the second reaction area;
  providing a blood sample and bringing the blood sample into contact with the first electrode set and the second electrode set;
  obtaining a hematocrit value by using the first electrode set;
  conducting a calibration to a linear equation related to an analyte concentration by using the hematocrit value to obtain a calibrated linear equation, wherein the linear equation related to the analyte concentration is y=ax+b, wherein y is the response value, a is a slope parameter, x is the analyte concentration, and b is an interception parameter, wherein the linear equation y=ax+b is a conversion equation of the response value and the analyte concentration when the hematocrit value of the blood sample is 0%;
  applying a voltage to the second electrode set to obtain a response value; and
  calculating an actual value of the analyte concentration by using the response value and the calibrated linear equation.

14. The method for detecting the analyte concentration as claimed in claim 13, wherein the method for conducting a calibration to the linear equation related to the analyte concentration by using the hematocrit value to obtain the calibrated linear equation comprises:
  obtaining a slope coefficient and an interception coefficient corresponding to the hematocrit value according to a reference table or a relationship equation; and
  conducting a calibration to the linear equation related to the analyte concentration by using the slope coefficient and the interception coefficient to obtain the calibrated linear equation.

15. The method for detecting the analyte concentration as claimed in claim 14, wherein the reference table comprises the slope coefficients and the interception coefficients corresponding to a plurality of hematocrit values, wherein the hematocrit values are in a range of 10% to 70%.

16. The method for detecting the analyte concentration as claimed in claim 14, wherein the calibrated linear equation is y=a'x+b', wherein y is the response value, a' is a slope parameter calibrated by the slope coefficient, x is the actual value of the analyte concentration, b' is an interception parameter calibrated by the interception coefficient.

17. The method for detecting the analyte concentration as claimed in claim 13, wherein the method for obtaining a hematocrit value by using the first electrode set comprises using amperometry, coulometry, potentiometry, voltammetry, impedance, or a combination thereof.

* * * * *